United States Patent [19]

Harnden et al.

[11] Patent Number: 4,736,029

[45] Date of Patent: Apr. 5, 1988

[54] PROCESS FOR PREPARING 2-AMINO-6-CHLOROPURINE

[75] Inventors: Michael R. Harnden, Horsham; Richard L. Jarvest, Surbiton, both of England

[73] Assignee: Beecham Pharmaceuticals, Epsom, England

[21] Appl. No.: 844,520

[22] Filed: Mar. 21, 1986

[30] Foreign Application Priority Data

Mar. 23, 1985 [GB] United Kingdom ............... 8507606

[51] Int. Cl.$^4$ .................... C07D 473/40; A61K 31/52
[52] U.S. Cl. ..................................... 544/277; 544/276
[58] Field of Search ................. 544/276, 277; 514/261

[56] References Cited

PUBLICATIONS

Lister, Purines p. 138 (1971), Wiley-Interscience.
Nasutavicus et al., J. Het. Chem., vol. 11, p. 77, (1974).
CA 79(21) 122316 (1973).
CA 103(23) 196046g (1985).

Primary Examiner—Nicholas Rizzo
Attorney, Agent, or Firm—Hopgood, Calimafde, Kalil, Blaustein & Judlowe

[57] ABSTRACT

A process for the preparation of the compound of formula (I):

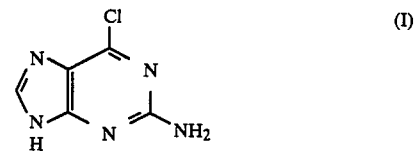

which process comprises reacting the compound of formula (II):

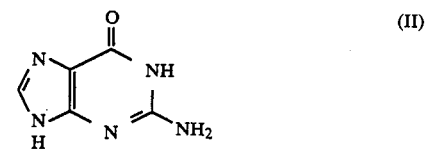

with a chlorinating agent in the presence of a phase transfer catalyst containing chloride ions.

8 Claims, No Drawings

PROCESS FOR PREPARING 2-AMINO-6-CHLOROPURINE

The present invention relates to a process for preparation of a compound useful as an intermediate in the preparation of pharmaceutical compounds.

The compound 2-amino-6-chloropurine of formula (I):

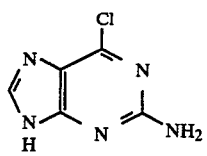

is a useful intermediate in the preparation of guanine nucleoside analogues, for example as described in EP-A-No. 141927.

The preparation of the compound of formula (I) by direct chlorination of the guanine of formula (II):

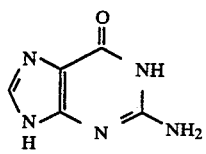

has been reported to be unsuccessful (ref. J. H. Lister, Purines p 138, Wiley - Interscience (1971) and W. A. Nasutavicus et al. J. Het. Chem. 11, 1974, p77).

A number of alternative preparations of the compound of formula (I) have been proposed but all these involve the conversion of the compound of formula (II) into the 6-thioguanine derivative of formula (III):

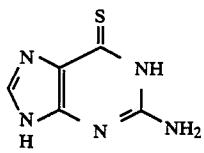

which is converted to the compound of formula (I) in one or two subsequent stages.

The compound of formula (III) is known to be mutagenic, and since several of the guanine nucleoside analogues derived from the compound of formula (I) are in use, or are of potential use as antiviral agents in man, the use of such a compound in synthesis of such agents is clearly undesirable.

A high yielding, one-stage process for the preparation of the compound of formula (I) has now been discovered which avoids the use of the intermediate of formula (III).

According to the present invention there is provided a process for preparing a compound of formula (I) as hereinbefore defined, which process comprises reacting a compound of formula (II) as hereinbefore defined with a chlorinating agent in the presence of a phase transfer catalyst containing chloride ions.

The reaction is preferably carried out in a polar inert organic solvent such as acetonitrile, tetrahydrofuran, dioxan, nitromethane, diglyme or dimethoxyethane. Acetonitrile is highly preferred.

Suitable phase transfer catalysts include tetrasubstituted ammonium chlorides. Examples of ammonium substituents include $C_{2-12}$ alkyl, usually $C_{2-4}$ alkyl, or phenyl or benzyl. Other possible phase transfer catalysts include tetra-substituted phosphonium chlorides wherein examples of the substitutents are as defined above for ammonium chlorides. Preferably the phase transfer catalyst is tetraethylammonium chloride.

The phase-transfer catalyst is preferably present in an amount of from 1 to 3 equivalents of the compound of formula (II) and preferably from 1 to 2 equivalents.

A preferred chlorinating agent is phosphorus oxychloride.

Preferably the chlorinating agent is present in an amount of from 2-10 preferably from 3-6 molar equivalents of the compound of formula (II).

The reaction may be effected in the presence of a weak base, such as a tertiary amine, for example N,N-dimethylaniline or diethylaniline. The base is usually present in an approximately molar equivalent amount with respect to the compound of formula (II). Alternatively, a catalytic amount of water may be added to the reaction mixture. When acetonitrile is the solvent, added base is not necessary.

The reaction is preferably carried out at an elevated temperature of from 30°–100° C., most preferably under reflux and/or with ultrasonication at 60°–70° C.

Preferably the reaction is allowed to proceed for a period of greater than half an hour, usually less than 30 hours.

The above described process has the advantage that it is suitable for large scale production of the compound of formula (I).

The following examples illustrate the invention.

EXAMPLE 1

2-Amino-6-chloropurine (Method A)

A mixture of guanine (4.5g, 30 mmol), tetraethylammonium chloride (7.46 g, 45 mmol monohydrate, pre-dried), phosphorus oxychloride (16.5 ml) and acetonitrile (60 ml) was heated under reflux for 70 minutes and allowed to cool. The solid material was filtered off and suspended in water. The aqueous mixture was brought to alkaline pH with aqueous sodium hydroxide and back to pH 7 with dilute hydrochloric acid. Continuous extraction (24 hours) with ethyl acetate afforded 2-amino-6-chloropurine as a white solid (2.12 g, 42%).

EXAMPLE 2

2-Amino-6-chloropurine (Method B)

A mixture of guanine (4.5 g, 30 mmol), tetraethylammonium chloride (30 mmol), phosphorus oxychloride (16.5 ml and acetonitrile (60 ml) was placed in a flask in an ultrasonic bath at 60° C. for 2 hours. The mixture was then heated under reflux for 90 minutes and allowed to cool. The solid material was filtered off and suspended in water. The aqueous mixture was brought to alkaline pH with aqueous sodium hydroxide and back to pH 7 with dilute hydrochloric acid. Continuous extraction with ethyl acetate afforded 2-amino-6-chloropurine as a white solid (1.55 g, 30%).

We claim:

1. A process for the preparation of the compound of formula (I):

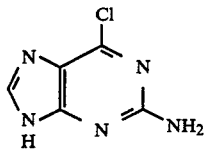

which process comprises reacting the compound of formula (II):

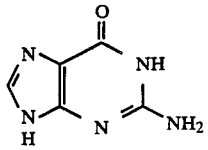

with a chlorinating agent in the presence of a phase transfer catalyst containing chloride ions.

2. A process according to claim 1 wherein the chlorinating agent is phosphorus oxychloride.

3. A process according to claim 1 wherein the chlorinating agent is present in an amount of 3–6 molar equivalents of the compound of formula (II).

4. A process according to claim 1 wherein the phase transfer catalyst is a tetra-substituted ammonium chloride.

5. A process according to claim 4 wherein the tetra-substituted ammonium chloride is a tetra-$C_{2-4}$ alkylammonium chloride.

6. A process according to claim 5 wherein the tetra-$C_{2-4}$ alkylammonium chloride is tetraethylammonium chloride.

7. A process according to claim 1 wherein the phase transfer catalyst is present in an amount of 1 to 2 equivalents.

8. A process according to claim 1 wherein the reaction of the compound of formula (II) is carried out in acetonitrile as solvent.

* * * * *

UNITED STATES PATENT AND TRADEMARK OFFICE
CERTIFICATE OF CORRECTION

PATENT NO. : 4,736,029

DATED : April 5, 1988

INVENTOR(S) : Michael Raymond Harnden and Richard L. Jarvest

It is certified that error appears in the above-identified patent and that said Letters Patent is hereby corrected as shown below:

At the first page of the patent, after "Assignee:", kindly delete "Beecham Pharmaceuticals, Epsom, England" and insert therefore -- Beecham Group plc, Middlesex, England--.

Signed and Sealed this

Tenth Day of January, 1989

*Attest:*

DONALD J. QUIGG

*Attesting Officer*          *Commissioner of Patents and Trademarks*